United States Patent [19]

Kaltenbrunner et al.

[11] Patent Number: 4,784,124

[45] Date of Patent: Nov. 15, 1988

[54] BONE IMPLANT FOR PROSTHESES AND TOOL FOR INSERTING THE IMPLANT INTO A BONE

[75] Inventors: Werner Kaltenbrunner, St. Marein; Rainer Kotz, Vienna, both of Austria

[73] Assignee: Vereinigte Edelstahlwerke Aktiengesellschaft (VEW), Vienna, Austria

[21] Appl. No.: 883,413

[22] Filed: Jul. 8, 1986

[30] Foreign Application Priority Data

Jul. 16, 1985 [AT] Austria .............................. 2097/85

[51] Int. Cl.⁴ .............................................. A61F 2/36
[52] U.S. Cl. .................................. 128/92 YZ; 623/23
[58] Field of Search ...... 128/92 VV, 92 VW, 92 YZ, 128/92 YY, 92 YK, 92 YW, 92 YV, 92 YT, 92 YG, 92 YQ; 623/19, 20, 22, 23

[56] References Cited

U.S. PATENT DOCUMENTS

| | | | |
|---|---|---|---|
| 2,719,522 | 10/1955 | Hudack | 623/23 |
| 3,067,740 | 12/1962 | Haboush | 623/23 |
| 3,977,398 | 8/1976 | Burnstein | 128/92 YZ |
| 3,996,625 | 12/1976 | Noiles | 623/22 |
| 4,430,761 | 2/1984 | Niederer et al. | 623/23 |
| 4,595,393 | 6/1986 | Anapliotis et al. | 623/22 |
| 4,653,487 | 3/1987 | Maale | 128/92 YZ |

FOREIGN PATENT DOCUMENTS

| | | | |
|---|---|---|---|
| 0145939 | 6/1985 | European Pat. Off. | 623/22 |
| 0209516 | 1/1987 | European Pat. Off. | 623/23 |
| 0498150 | 9/1954 | Italy | 623/23 |

Primary Examiner—Stephen C. Pellegrino
Assistant Examiner—Ralph Lewis
Attorney, Agent, or Firm—Werner W. Kleeman

[57] ABSTRACT

The bone implant for prostheses, particularly joints or joint members, preferably joints of the human locomotor system and especially the walking system, contains a shaft insertable into a cavity in a bone. The shaft has a total cross-section increasing from its diaphysis-associated distal end to its metaphysis-associated proximal end. Preferably, The shaft possesses in the region of the metaphysis-associated proximal end an integrally formed or separate intermediate piece at which the joint or joint member can be arranged. The shaft is preferably immediately and securely anchored in the bone and particularly is made of a metallic material. The shaft possesses an oblong rotationally symmetrical shaft body having an outer surface generated by, if desired, a longitudinally curved or preferably a substantially straight generatrix. The shaft body substantially has the shape of a truncated cone. Its outer surface can be contracted with the bone without the presence of a bonding agent and possesses a plurality of projections extending substantially parallel to the generatrix generating the outer surface. The projections preferably extend along the total length of the shaft body and are preferably mutually similar. The projections have edges extending preferably radially outwardly from the main axis of the shaft body, and preferably have the form of a knife edge.

50 Claims, 1 Drawing Sheet

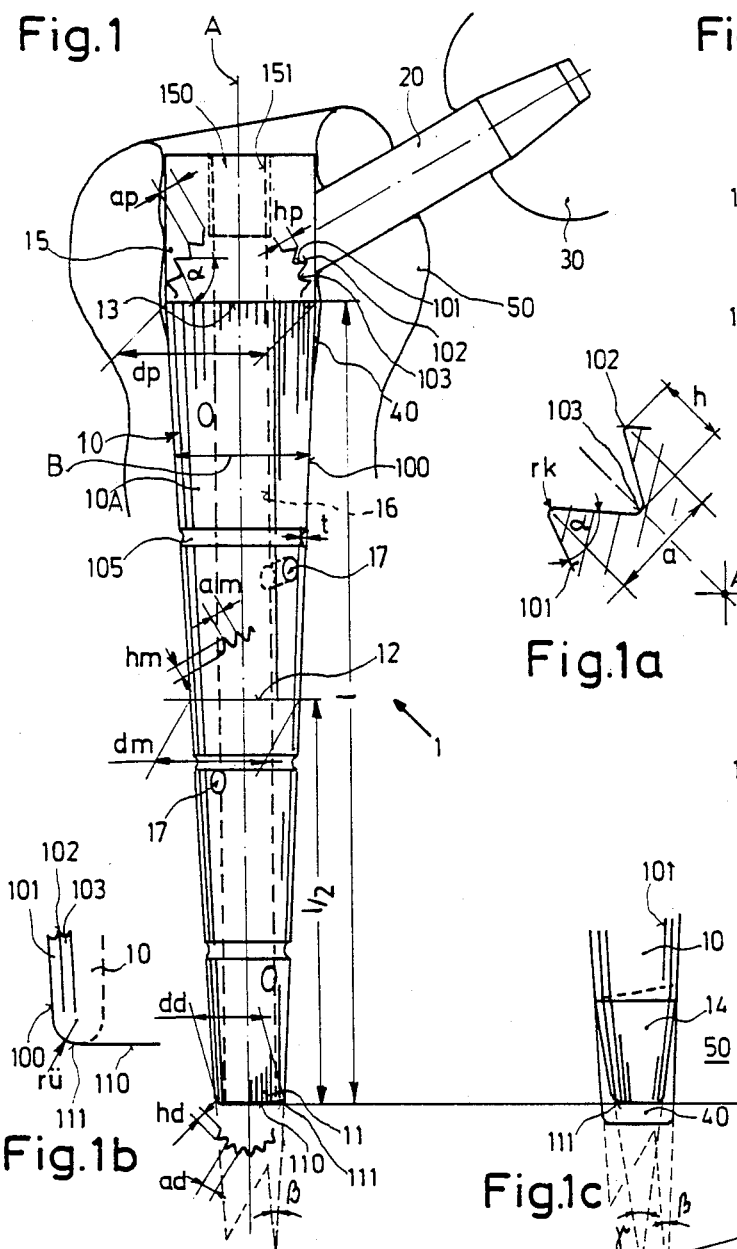
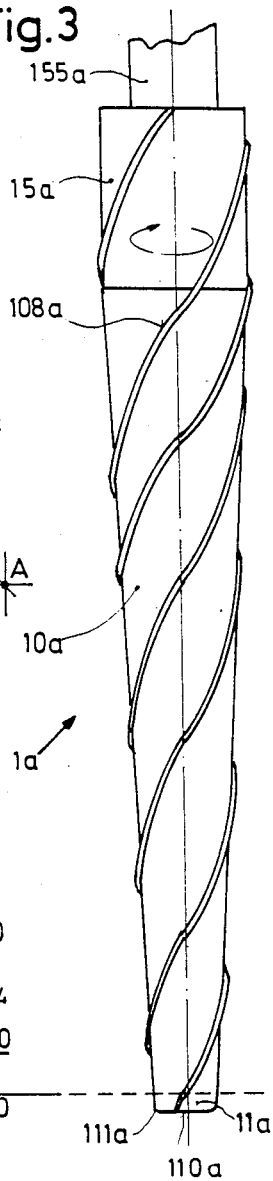
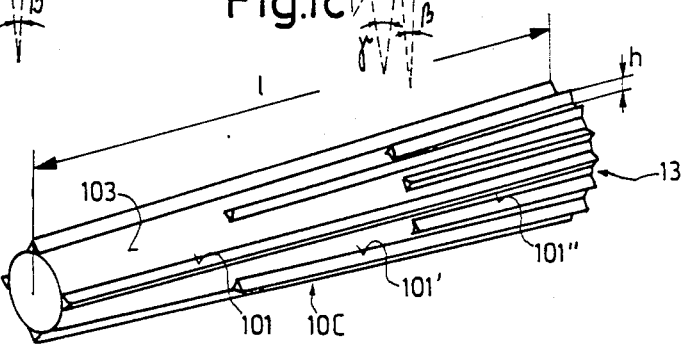

BONE IMPLANT FOR PROSTHESES AND TOOL FOR INSERTING THE IMPLANT INTO A BONE

BACKGROUND OF THE INVENTION

The present invention relates to a new and improved construction of a bone implant for a prosthesis, particularly for a joint or joint member of the human locomotor, especially walking system.

The present invention also relates to a new and improved construction of a tool for preparing a bone especially for bonding agent-free insertion of a prosthesis bone implant having a shaft with a shaft body of a predetermined shape extending between a metaphysis-associated proximal end and a diaphysis-associated distal end of the shaft body.

In its more particular aspects, the present invention specifically relates to a new and improved construction of a bone implant for a prosthesis, specifically an endoprosthesis, particularly for a joint or joint member of the human locomotor, especially walking system and which bone implant contains a shaft which is to be inserted into a cavity formed in a bone, preferably a long bone. The shaft has a total cross-sectional area which increases from its diaphysis-associated distal end toward its metaphysis-associated proximal end. Preferably in the region of the metaphyseal or proximal end, the shaft possesses an intermediate piece or member at which a joint or joint member is arranged or arrangeable. The intermediate piece or member is formed integrally with or separately from the shaft.

A large number of such implantable prostheses, particularly for hip joints, have become known. For the shaft to be anchored in the bone there have been proposed various biocompatible materials, i.e. materials which are compatible with both tissue and body fluids and which are not corrodable by the tissue and the body fluid, such as in particular metals, for example, high alloyed steels, special alloys, ceramics, fiber-plastic composites, wood or the like. Despite all the diversity of construction, the known shafts or anchoring members for such prostheses generally include an oblong shaft body which is inserted into the bone. A joint member, for example, a joint cup, a joint plane, a joint sphere or condyle or a joint roll or trochlea is arranged at the proximal end of the shaft either directly or by means of a connecting or intermediate piece or member provided to maintain predetermined positional angles and spacings. The connecting or intermediate piece or member frequently is formed in one piece with the shaft with which the related joint member is connectable preferably in a detachable manner. The materials of the joint member and of the prosthesis shaft are not identical in most of the cases due to their different functions. Most of the oblong joint prosthesis shafts for insertion particularly into long bones, are constructed with a predetermined shape such that the cross-section decreases from the proximal end region to the distal end region thus enabling an adaptation to natural conditions such as in particular the shape of the cavity formed in the bone. The material removal during preparation of the cavity for receiving the implant shaft is thereby minimized.

For the purpose of anchoring implants in a bone there have become known either the employment of bonding agents, for example, formed on the basis of plastic materials or a bonding agent-free anchoring technique. By means of this direct anchoring technique there can be avoided the problems resulting from heat development and tissue incompatibility of the bonding agent. It is intended that, after insertion of the shaft or shaft member, if possible, no longer period of time has to be spent for incorporation or settling of such shaft or shaft member into the bone and that a secure or stable connection is provided between the shaft and the bone immediately after insertion of the bone implant.

The commercially available bone implant shafts used in practice normally do not have a rotationally symmetric cross-section. In order to provide an anchoring which is secured against rotation, the conventional bone implant shafts possess a multi-angular or multi-corner, preferably rectangular cross-section with rounded edges and with longitudinal grooves, recesses, openings or the like. For adaptation to the bone, many prior art constructions contain a longitudinal curvature. The cavity for receiving the shaft is substantially prepared in such a manner, that a rasp, a reamer or the like which is formed substantially in correspondence to the shape of the shaft to be implanted, is oscillatingly moved, for example, by means of a pneumatic drive, and driven into the bone toward the diaphysis. Although already in use for a long time, this technique does not permit preparing cavities whose walls precisely come into snug contact with the outer or bone contact surface of the shaft over large areas or the entire surface area of such walls. On the contrary, these known implant shafts of various shapes contact the wall of the cavity only at a few locations and over relatively small areas. However, at these very locations the mechanical forces are introduced via zones of relatively small surface area and thus at high pressure load or point load. Such pressure point loads or peaks, however, are known to cause a disturbance in the biological equilibrium in the bone and the bone accordingly reacts such that there results precisely at these locations of increased pressure load a degradation of the bone substance and thus a weakening of the cortex which leads to a loosening of the shaft fit.

Furthermore, there is known, for example, from German Patent Publication No. 2,049,111, a prosthesis member containing a short conical implant shaft with a substantially smooth surface. According to this publication, an adaptation of the shaft modulus of elasticity to that of the bone is intended to be achieved by means of an appropriate mechanism. The construction shown in this publication cannot achieve a secure anchoring against loosening and rotation and cannot be loaded for a longer period of time.

SUMMARY OF THE INVENTION

Therefore, with the foregoing in mind it is a primary object of the present invention to provide a new and improved construction of a bone implant for a prosthesis, particularly for a joint or joint member of the human locomotor, especially walking system and which bone implant permits a simplified and considerably more precise technique for preparing the cavity for receiving the implant in the bone and at the same time avoids the occurrence of pressure point loads or peaks by uniformly introducing the mechanical load and the forces into the bone via the greatest possible contact areas which are in snug engagement from the beginning.

A further important object of the present invention aims at providing a new and improved construction of a bone implant for a prosthesis, particularly for a joint or joint member of the human locomotor, especially walking system and which bone implant provides highest security against rotation about the bone implant axis, excellent physiological compatibility and high suitability for long-time service.

Now in order to implement these and still further objects of the present invention, which will become more readily apparent as the description proceeds, the bone implant of the present development is manifested by the features that, the shaft can be preferably immediately and securely anchored in the bone and particularly is made of a metallic material. The shaft possesses an oblong rotationally symmetric shaft body having an outer surface generated by, if desired, a longitudinally curved generatrix, however, preferably by a substantially straight generatrix. The shaft body preferably has the shape of a truncated cone. The outer or bone contact surface of the shaft body can be contacted, preferably without the use of a bonding agent, with the bone and is provided with a plurality of projections extending substantially parallel to the generatrix of the outer surface or the shaft body. The projections preferably extend substantially along the total length of the shaft body and are preferably mutually similar. The projections protrude substantially outwardly from the main axis of the shaft, preferably radially, and have knife like edges.

Due to the rotationally symmetrical, at least substantially conical construction of the shaft body, there is achieved a considerable simplification in the preparation of the cavity for the insertion of the shaft into the bone. The cavity can be prepared by means of a cutting or milling tool corresponding to the respective shaft dimensions in a highly precise manner with respect to position and depth and without oscillating milling or the like. Since high conformity between the conicity of the cavity wall and that of the outer or bone contact surface of the shaft body can be obtained, there is guaranteed a basically significantly enlarged contact area with the bone. Surprisingly, the edges of the projections do not prohibit a snug fit of the shaft in the bone with the formation of large contact areas and at the same time are capable of guaranteeing highest security against rotation. During the driving-in operation on the shaft, the edges laterally displace the bone substance and slightly cut into the cortex. Thereafter the biological equilibrium can be restored in a short time. It could be demonstrated that any danger of a wedge-like splitting or bursting of the bone as observed, for example, when using a more extended surface area construction of the anchoring elements, is completely avoided. Due to the rotationally symmetric conical construction there is guaranteed a centering carving-out operation during preparation of the cavity and a self-centering insertion of the shaft into the bone.

In the inventive construction there exists practically in all regions of the shaft a snug engagement of the outer or bone contact surface of the shaft with the bone, even when there occur settling reactions or movements. It has been found, however, that such settling movements remain within the millimeter range at the most. By means of the cone the forces acting substantially in the direction of the bone extension are introduced into the bone via a relatively large surface area and obliquely with small transverse vectors, thus avoiding pressure point loads or peaks and the concomitant danger of local degradation of bone substance in the mechanically higher loaded contact regions of the prosthesis with the bone.

It has further been shown that the construction of the outer or bone contact surface according to the invention also guarantees high security against undesired withdrawal of the shaft from the bone. In addition thereto and, by means of the edges of the projections, there can be stimulated the settling or incorporating process of the bone implant, the immediate and secure anchoring of the bone implant being realized immediately after the implantation without any time required for the settling or incorporation of the bone implant. Due to the arrangement of a plurality of lengthwise extending projections there can be ensured a lengthwise transport and a lengthwise exchange of the biological fluid at the outer or bone contact surface in the region of the associated groove bases and thus establishment and maintenance of the biological equilibrium also in the lengthwise direction. The full area contact obtainable in spite of or by means of the edges of the projections right after the driving-in operation is capable of preventing loosening of the prosthesis even under strong transverse loads accompanied by a lever action.

It is further emphasized that the novel and inventive bone implant, although foreseeably mostly used for replacement of part of the human femur, is quite suitable, for example, for knee joints, but also for other human joints, for example, cubital joints or shoulder joints because such bone implants are adaptable to different applications substantially via the cone dimension. Such multiple applications are recommended particularly as a consequence of the surprisingly high security of the novel and inventive shaft prosthesis or bone implant against withdrawal.

Particularly in view of the inner structure of the bone and hence the long-time stability and strength of the implant-bone-connection and further for minimizing the amount of bone substance which must be removed in order to prepare the implant cavity in which the bone implant is fixedly anchored, it is preferred that the outer or bone contact surface has a predetermined conicity or the edges of the projections projecting from the shaft body have a predetermined inclination. Such conicity or inclination is determined by the ratio between the difference of the diameters measured at the proximal end and at the distal end of the shaft and the length of the shaft body. This ratio has a value substantially in the range of about 1:4 to about 1:20, particularly about 1:6 to about 1:15 and preferably about 1:8 to about 1:12. When adhering to this conicity there is achieved a particularly balanced relationship between radially acting forces and the absorption capacity of the bone for such forces and the necessary removal of bone substance for the cavity can be maintained small. In practice, the abovementioned ratio in the range of about 1:10 has proved particularly successful for femur implants.

For the physiology of the bone and further for increasing the security against rotation about the lengthwise shaft axis and against unintentional extraction of the bone implant, a predetermined value has been found advantageous for the ratio between the distance or spacing between two adjacent projections or, if desired, their edges to the central diameter of the shaft body. Such predetermined value of the aforementioned ratio substantially is in the range of about 1:5 to about 1:30, preferably about 1:10 to about 1:20, particularly about 1:10 through 1:15. For practical purposes this means that a femur joint prosthesis shaft for an adult may have, for example, a proximal cone diameter substantially in the range of 20 to about 30 mm and a distal cone diameter substantially in the range of about 10 to about 15 mm at a length substantially in the range of 100 to about 160 mm and a distance between two adjacent projections at the proximal, namely the broad end of the shaft substantially in the range of about 0.7 to about 1.1 mm.

For alimentation of the bone near the bone implant and the material exchange in longitudinal direction as well as for securing the anchoring against rotation, it is advantageous when the ratio of the height of the projections to the central diameter of the shaft body is ensured to have a value substantially in the range of about 1:5 to about 1:30, particularly about 1:10 to about 1:20.

Particularly for assuring from the start, i.e. immediately after insertion or implantation of the prosthesis a secure conical plug connection which is initially accomplished with penetration of the edges into the bone substance accompanied by slight displacement of such bone substance, the edges of the projections which are directed outwardly away from the main shaft axis, advantageously possess an edge radius substantially in the range of about 10 to about 100 micrometers, particularly of about 20 to about 50 micrometers.

Regarding both the technique during operation and the post-operative healing of the prosthesis it has proved of particular advantage that the projections, at least in the region close to their edges, are constructed with a substantially triangular shape, if desired, with two equal sides and with an edge angle α substantially in the range of about 30° to about 150°, particularly about 60° to about 120°, preferably in the range of about 90°. Furthermore, this does not cause any specific manufacturing complications.

Furthermore and constituting an advantageous design, the regions, particularly the depressions between the projections are rounded preferably with a radius of curvature which is greater than the aforementioned edge radius. Clogging of the longitudinal grooves, for example, by such bone substance particles originate from the operation thus can be prevented.

With respect to manufacturing considerations, but also with regard to the introduction of forces and their distribution, the height of the projections advantageously decreases from the proximal end toward the distal end of the shaft.

In order to obtain an entirely snug fit of the bone implant in the bone immediately after implantation and to maintain the surface load particularly uniform and small the height of the projections advantageously is substantially constant from the proximal end to the distal end of the shaft and the shaft body possesses a number of continuous projections in correspondence with the shaft diameter substantially at the distal shaft end. Further preferably similar projections are arranged between the aforementioned projections and extend, starting from the proximal shaft end, over a shorter distance to the distal shaft end.

However, this construction requires more elaborate manufacture. For the insertion of this bone implant there is first placed into the bone the rotationally symmetric or symmetrical, truncated cone-shaped cavity. Thereafter and for augmenting the precision and immediate anchoring security, longitudinal channels or furrows of a predetermined length corresponding to the length of the edges of the projections protruding from the shaft body, can be formed in the conical wall of the bone cavity by means of an oscillating material removing tool like, for example, a reamer provided with cutting edges which correspond to the various edges of the projections protruding outwardly from the shaft body, for positioning the related projections.

In accordance with a further advantageous variant the shaft body possesses at the distal shaft end a section having an outer surface substantially in the shape of a truncated cone, if desired, in a skewed arrangement and with a greater cone angle of its generatrix than the generatrix cone angle associated with the shaft body itself. There is thus prevented a lateral penetration of the distal shaft edge into the cortex when the bone implant is not quite correctly inserted and an abrupt weakening caused thereby. In this manner there is ensured in the distal region at the periphery of the distal end a smooth circumferential transition from the bone implant to the bone without the formation of any horizontal notch locations.

Preferably, the shaft body possesses at its proximal end a substantially cylindrical extension which, if desired, contains an anchoring element, for example, an internal thread. By means of such proximal extension there can be avoided unnecessary spongia removal from the metaphysis and lateral displacement of the shaft end. Also, such anchoring element significantly facilitates later operative removal of the bone implant.

Furthermore, the shaft body advantageously possesses a substantially cylindrical cavity which opens at least toward the distal shaft end. There are thus ensured a saving in weight and improved alimentation of the tissue due to the inner free longitudinal flow of the body fluids.

This body fluid flow and also the settling or incorporation of the bone implant can be further assisted by a shaft body which preferably possesses substantially radial connecting passages between the cavity and the outer bone contact surface.

Advantageously, a decrease in notching action and a type of circumferentially elastic distal shaft end region of a bone implant shaft containing a cavity, when such bone implant shaft is seated in the bone, can be achieved with a construction conceived in the manner of an annular lip and thereby a reduction and improved distribution of pressure loads, for example, in the event of lever-type stress. Such construction contains a substantially rounded transition of the outer or bone contact surface to the distal shaft end surface, particularly, to the cavity in the shaft body, preferably with a radius substantially in the range of about 0.2 to about 0.8 mm, particularly in the range of about 0.5 mm.

In accordance with a further preferred construction, the outer bone or contact surface possesses circumferential grooves which preferably extend around the entire circumference and along predetermined planes extending substantially perpendicular to the main shaft axis.

Such circumferential grooves preferably are formed with round edges and, if desired, with round bases. There are thus ensured particularly high security against tensile load and an enhancement of the horizontal-peripheral exchange of body fluids as well as the possibility of circumferential tissue growth.

The number of circumferential grooves preferably is limited to a number below about 10, and preferably a number below about 5 is considered sufficient.

With the view of achieving particularly good anchoring of the bone implant and enhanced peripheral exchange of body fluids the depth of the circumferential grooves is favorably at least equal to the height of the longitudinally extending projections at those locations at which the projections are present.

Furthermore and advantageously the shaft body is manufactured from metallic material, particularly by forging, and in one piece with an intermediate piece or member for the arrangement thereat of a joint or a joint member. There can thus be achieved manufacturing simplicity conjointly with high strength of the connection of the bone implant shaft, for example, with a laterally protruding intermediate piece or neck piece suitable for receiving, for example, a coated joint sphere or condyle or the like. This is due to the fact that there can be obtained during forging a continuous flow of the material fibers from the shaft into the intermediate piece or member, whereby smooth introduction of the forces into the bone implant shaft and into the bone is ensured.

As alluded to above, the invention is not only concerned with the aforementioned bone implant construction aspects, but also relates to a new and improved construction of a tool for preparing a bone, especially for bonding agent-free insertion of a prosthesis bone implant of the hereinabove referred-to construction.

In its more particular aspects, the construction of the inventive tool is distinguished by a tool body, particularly a milling body, which has the shape of a truncated cone substantially corresponding, particularly with respect to conicity, to the shaft of the bone implant intended to be inserted into the respective bone.

The tool body is rotatable, preferably by pneumatic rotational drive means, and possesses at its outer surface a plurality, preferably an odd number of substantially helically extending cutting edges. Preferably, the tool body has an extension at its distal end; the extension is also provided with cutting edges and penetrates diaphyseally deeper into the bone than the bone implant which is later inserted into the bone. Due to this construction of the tool there is achieved a particularly good positionally controllable concentric run of the tool within the hard bone and there is possible the attainment of an extremely short period of time for preparing the cavity for the subsequent accommodation of the bone implant. A later step-like notching or scoring of the bone by the distal shaft end is substantially avoidable since due to the aforementioned extension the cavity of identical conicity is driven somewhat farther into the bone than the ultimately inserted bone implant shaft.

The cutting edges of the tool are favorably asymmetrically distributed around the cross-section of the tool body and enclose different angles which differ from each other by angles substantially in the range of about 0.5° to about 3°.

Furthermore the distal end of the tool body, particularly the milling body and preferably the related regions of the cutting edges, are preferably constructed with a substantially rounded shape. There is thus achieved a particularly good centering run of the tool and thereby high precision and adaptation of the cavity in the bone to the shape of the prosthesis or bone implant shaft.

The tool further and advantageously possesses in its proximal region a substantially cylindrical extension provided with cutting edges which preferably constitute a continuation of the cutting edges at the tool or milling body. There thus can be avoided unnecessary removal of bone substance in the metaphysis region during preparation of the cavity which is intended to receive the bone implant.

BRIEF DESCRIPTION OF THE DRAWINGS

The invention will be better understood and objects other than those set forth above will become apparent when consideration is given to the following detailed description thereof. Such description makes reference to the annexed drawings wherein throughout the various figures of the drawings; there have been generally used the same reference characters to denote the same or analogous components and wherein:

FIG. 1 is a side view of a first exemplary embodiment of the inventive bone implant for replacing a femur joint;

FIG. 1a is a section through the edge of a projection protruding or projecting from the shaft body of the bone implant shown in FIG. 1;

FIG. 1b is a side view of a detail of the distal end of a hollow shaft body of the bone implant shown in FIG. 1;

FIG. 1c is a side view of the distal end of the shaft body in the implanted condition of the bone implant shown in FIG. 1;

FIG. 2 is a partial perspective view of a second embodiment of the inventive bone implant; and FIG. 3 is a side view of an exemplary embodiment of the inventive tool for preparing in a bone a cavity for receiving the bone implant shown in FIGS. 1 and 2.

DETAILED DESCRIPTION OF THE PREFERRED EMBODIMENTS

Describing now the drawings, it is to be understood that only enough of the construction of the bone implant and the tool for preparing in a bone a cavity for receiving such bone implant, have been shown as needed for those skilled in the art to readily understand the underlying principles and concepts of the present development, while simplifying the showing of the drawings. Turning attention now specifically to FIG. 1 of the drawings, there has been shown in a side view an exemplary embodiment of the inventive bone implant or prosthesis, especially endoprosthesis generally designated by the reference numeral 1. This bone implant 1 contains a shaft 10 which defines a main axis A. The shaft 10 includes a distal end 11 and a proximal end 13 respectively associated with the diaphysis and the metaphysis of the bone into which the bone implant 1 containing the shaft 10 is inserted. The shaft 10 further defines a total cross-sectional area B which increases from the distal end 11 to the proximal end 12 of such shaft 10.

The shaft 10 possess a shaft body 10A of oblong substantially rotationally symmetric shape which is defined by a generatrix generating an outer surface 100 of the shaft body 10A. This outer surface 100 of the shaft body 10A constitutes the bone contact surface of the shaft 10 and the generatrix which generates such outer surface or bone contact surface 100 extends along a substantially straight line. As a result, the shaft body 10A substantially assumes the predetermined shape of a truncated cone.

The shaft 10 is provided at one side with an obliquely attached intermediate piece or member 20 at which a joint sphere or condyle 30 can be arranged. The outer or bone contact surface 100 of the bone implant shaft 10 and which surface 100 contacts the cavity 40 of the bone 50 in the implanted condition possesses projections 101 which extend substantially over the total length of the shaft 10. Edges 102 of the projections 101 are directed outwardly, in the illustrated embodiment radially away from the shaft'S main axis A. Each edge 102 defines an edge angle α which may assume any appropriate value substantially in the range of about 30° to about 150°, particularly about 60° to about 120°. In the illustrated embodiment the edge angle is 75° and such edge angle preferably has a value in the region of about 90°. Each intermediate region or space 103 between the projections 101 is rounded at the base of the thus formed depression or groove. The edges 102 of the projections 101, as shown in detail in FIG. 1a, assume a knife edge-like shape defining an edge radius rk substantially in the range of, for example, about 10 to about 100 micrometers, in the illustrated embodiment substantially in the range of about 20 to about 50 micrometers. The spacing a of the edges, for example, at the shaft center 12 is designated am and has a value of, for instance 0.8 mm, at the proximal shaft end 13 is designated ap and at the distal shaft end 11 is designated ad. The height h of the projections 101 correspondingly has the respective values of hm, hp and hd at the aforementioned shaft locations. The spacing a between the projections 101 as well as their height h decrease from the proximal shaft end 13 to the distal shaft end 11.

The conicity of the shaft body 10A is determined by a predetermined ratio of the difference between the shaft diameter dd at the distal end 11 and the shaft diameter dp at the proximal end 13 of the shaft 10 to the predetermined total length l of the shaft body 10A. This ratio may assume any appropriate value substantially in the range of about 1:4 to about 1:20, particularly about 1:6 to about 1:15. Preferably the ratio has a value substantially in the range of about 1:8 to about 1:12 and amounts to a value of about 1:10 in the illustrated embodiment. The shaft diameter at the shaft center 12 is designated by dm.

In addition to the longitudinal projections 101 the shaft body 10A may also contain circumferential grooves 105 which preferably extend around the entire circumference and have a predetermined depth t which may be greater than the height h of the projections 101 in the region of the grooves 105.

Substantially at its proximal end 13, the shaft 10 meshes or merges with a smooth cylindrical extension 15 containing a bore 150 with a thread 151 which constitutes an anchoring element facilitating the anchoring of an extraction tool in the case of an operative removal of the bone implant 1 from the bone 50. The shaft body 10A as well s the intermediate m ember 20 are advantageously manfactured from metallic material, particularly by forging and in one piece.

The bone implant shaft 10 or shaft body 10A, as shown and indicated by broken lines, may further possess an empty space or cavity 16 which is of substantially cylindrical shape in the illustrated embodiment. As evident from FIG. 1b, the radius rü of a transition region 111 from the outer or bone contact surface 100 to the empty space or cavity 16 which continuously extends to the bore 150 in the illustrated embodiment may be substantially identical to the radius of a transition region to a distal end surface 110 in the absence of an empty space or cavity 16 in the shaft 10. From the empty space or cavity 16 there may extend passages or openings 17 toward the outer or bone contact surface 100, as shown in FIG. 1 by dotted lines.

From FIG. 1c it will be apparent that, if desired, the distal end 11 of the shaft 10 may be provided with a cone or substantially conically shaped extension 14 which has a greater cone angle γ than the cone angle β of the shaft 10 itself. As indicated in broken lines, the cone or extension 14 may be present in a skewed arrangement. The cone or extension 14 can assist in preventing, with increased reliability, a local unilateral notching or scoring of the cortex by the distal edge 111 of the shaft 10 during the driving-in operation.

In the second exemplary embodiment of the inventive bone implant 1 which is schematically shown in FIG. 2, the bone implant shaft body 10 substantially is of the same basic or principle construction and differs from the shaft body 10A shown in FIG. 1 essentially by continuous projections 101 of a height h which, however, is substantially constant along the length l of the shaft 10. Towards the proximal end 13 there extend intermediate projections 101' in the widening grooves 103. Still farther in this direction toward the proximal end 13 there start further intermediate projections 101''. Preferably all such projections 101, 101' and 101'' are substantially similarly constructed.

FIG. 3 shows a side view of an exemplary embodiment of the inventive tool 1a for preparing in a bone a cavity for receiving a bone implant shaft of the type as shown, for example, in FIG. 1. The tool 1a includes a tool or milling body 10a having a contour substantially in the shape of a truncated cone and substantially identical to the bone implant shaft 10 shown in FIG. 1. In comparison thereto the cone of the shaft 10a is somewhat prolonged by an extension 11a which has, in its contour, a rounded transition region 111a towards the distal end face 110a. At the proximal end the tool or milling body 10a possesses a substantially cylindrical extension 15a essentially corresponding to the extension 15 of the shaft 10 shown in FIG. 1. The extension 15a possesses a prolongation 155a provided with a connecting element (not shown for connecting with drive means like, for example, pneumatic drive means for rotationally driving the tool or milling body 10a. Along each of the proximal extension 15a, the substantially conical tool or milling body 10a and its distal extension 11a there extend a predetermined number of cutting edges 108a of rather large helical pitch. Preferably and in the illustrated embodiment an odd number, for example, seven cutting edges 108a continuously extend along the aforementioned members. Relative to the cross-section of the tool 1a the continuous cutting edges 108a are asymmetrically distributed, i.e. enclose mutually different angles. Furthermore, the direction of the helix is opposite to the direction of rotation because otherwise the tool or milling tool la would be screwed into the bone.

A tool like the tool or milling tool la described hereinbefore enables high precision during preparation of the cavity in the bone for receiving a bone implant and significantly reduces the time required therefor.

While there are shown and described present preferred embodiments of the invention, it is to be distinctly understood that the invention is not limited thereto, but may be otherwise variously embodied and practiced within the scope of the following claims.

Accordingly, what we claim is:

1. A bone implant for a prostheses, particularly for a joint or joint member of the human locomotor, especially walking system, comprising:
   a shaft for insertion into a cavity formed in a bone of the locomotor system;

said shaft including a distal end associated with the diaphysis of said bone and a proximal end associated with the metaphysis of said bone;

said shaft possessing a shaft body;

said shaft body having an outer surface substantially in the shape of the outer surface of a truncated cone;

said shaft body containing an inner cavity open at least at said distal end of said shaft;

said shaft defining a main axis;

a plurality of projections outwardly protruding from said outer surface of said shaft body and extending along said outer surface in the direction of the main axis of said shaft from said proximal end at least close to said distal end of said shaft;

wherein each of said projections outwardly protruding from said outer surface of said shaft body protrudes to a maximum predetermined height at the proximal end to a minimum predetermined height at the distal end of said shaft;

each said projection having at least one edge directed substantially outwardly away from said main axis of said shaft; and said outer surface of said shaft body and said projections outwardly protruding from said outer surface providing a substantially full area contact with the bone upon insertion into an implant cavity formed in the bone.

2. The bone implant as defined in claim 1, wherein: the proximal end of said shaft is arranged in the region of the joint member.

3. The bone implant as defined in claim 2, further including:

an intermediate member interconnecting said proximal end of said shaft and the joint member.

4. The bone implant as defined in claim 3, wherein: said intermediate member is integrally formed with said proximal end of said shaft.

5. The bone implant as defined in claim 4, wherein: said integrally formed intermediate member for the arrangement at the joint member and said shaft essentially consists of a metallic material.

6. The bone implant as defined in claim 5, wherein: said integrally formed intermediate member for arrangement at the joint member and the shaft constituting a forged metallic member.

7. The bone implant as defined in claim 1, wherein: said shaft is structured for immediate and secure anchoring in the bone.

8. The bone implant as defined in claim 1, wherein: said shaft essentially consists of a metallic material.

9. The bone implant as defined in claim 1, wherein: said shaft body possesses a predetermined total length between said proximal end and said distal end of said shaft; and said plurality of projections extending essentially along said predetermined total length of said shaft body from said proximal end to said distal end of said shaft.

10. The bone implant as defined in claim 9, wherein: said outer surface of said shaft body constitutes a bone contact surface and defines a predetermined conicity;

said at least one edge of each said projection extending at a predetermined inclination along said predetermined total length of said shaft body and thereby defining different diameters at the proximal end and the distal end of said shaft and thereby a predetermined conicity of said projections;

said predetermined conicity of said outer surface of said shaft body and said predetermined conicity of said at least one edge of said projections being determined by the ratio of the difference formed between said different diameters of said bone contact surface and of said at least one edge of each said projection to said predetermined total length of said shaft body; and said ratio assuming a value in the range of about 1:4 and 1:20.

11. The bone implant as defined in claim 10, wherein: said predetermined ratio formed between the different diameters of said bone contact surface and of said at least one edge of each said projection to said predetermined total length of said shaft body assumes a value in the range of about 1:6 and about 1:15.

12. The bone implant as defined in claim 10, wherein: said predetermined ratio formed between said different diameters of said bone contact surface and of said at least one edge of each said projection to said total length of said predetermined shaft body assumes a value in the range of about 1:8 to about 1:12.

13. The bone implant as defined in claim 9, wherein; said outer surface of said shaft body constitutes a bone contact surface;

said bone contact surface containing a predetermined number of grooves distributed along said predetermined total length of said shaft body; and each one of said predetermined number of grooves in said bone contact surface extending in a plane which is arranged substantially perpendicular to said main axis of said shaft.

14. The bone implant as defined in claim 13, wherein: said shaft body has a circumferential surface defined by said bone contact surface; and said predetermined number of grooves substantially extends around the entire circumferential surface of said shaft body.

15. The bone implant as defined in claim 14, wherein: said predetermined number of circumferentially extending grooves amounts to a number less than 10.

16. The bone implant as defined in claim 15 wherein: said predetermined number of circumferentially extending grooves amounts to a number less than 5.

17. The bone implant as defined in claim 13, wherein: each one said circumferentially extending grooves in said bone contact surface possesses a predetermined depth and;

said projections extending from said outer surface of said shaft body possessing a predetermined height in the region of said circumferentially extending grooves; and said predetermined depth of each one of said predetermined number of grooves being at least equal to said predetermined height of said projections outwardly protruding from said outer surface of said shaft body in the region of said grooves.

18. The bone implant as defined in claim 13 wherein: each one of said predetermined number of grooves provided in said bone contact defines a predetermined number of edges; and said predetermined number of edges defined by said grooves constituting substantially rounded edges.

19. The bone implant as defined in claim 13 wherein:

each one of said predetermined number of grooves provided in said bone contact surface is bounded by a groove base.

said groove base of each one of said predetermined number of grooves constituting a substantially rounded groove base.

20. The bone implant as defined in claim 1, wherein:
said projections at the outer surface of said shaft body possess mutually similar shapes.

21. The bone implant as defined in claim 1, wherein:
said at least one edge of each said projection extends substantially radially outwardly from said main axis of said shaft.

22. The bone implant as defined in claim 1, wherein:
said at least one edge of said projection possesses a substantially knife edge-like shape.

23. The bone implant as defined in claim 1, wherein;
two adjacent ones of said plurality of projections outwardly protruding from the outer surface of said shaft body are arranged at a predetermined spacing from each other;
said shaft body defining a central diameter;
said spacing between said two adjacent projections defining a predetermined ratio to said central diameter of said shaft body; and
said predetermined ratio of said spacing between said two adjacent projections to said central diameter of said shaft body assuming a value in the range of about 1:15 to about 1:30.

24. The bone implant as claimed in claim 23 wherein:
said predetermined ratio between said spacing between said two adjacent projections and said central diameter of said shaft body assuming a value in the range of about 1:10 to about 1:20.

25. The bone implant as defined in claim 23, wherein:
said predetermined ratio between said spacing of said two adjacent projections and said central diameter of said shaft body assuming a value in the range of about 1:10 to about 1:15.

26. The bone implant as defined in claim 23, wherein:
said spacing between two adjacent projections is defined between the edges associated with said two adjacent projections.

27. The bone implant as defined in claim 1, wherein:
said shaft body defining a central diameter;
said height of said projections and said central diameter of said shaft body defining a predetermined ratio; and
said predetermined ratio between said height of said projections and said central diameter of said shaft body assuming a value in the range of about 1:5 to about 1:30.

28. The bone implant as defined in claim 27, wherein:
said predetermined ratio between said height of said projections and said central diameter of said shaft body assumes a value in the range of about 1:10 to about 1:20.

29. The bone implant as defined in claim 1, wherein:
said at least one edge of each said projection protruding outwardly from said main surface of said shaft possessing a predetermined edge radius; and
said predetermined edge radius having a value substantially in the range of about 10 to about 100 micrometers.

30. The bone implant as defined in claim 29, wherein:
said predetermined edge radius of said at least one edge of each said projection assumes a value substantially in the range of about 20 to about 50 micrometers.

31. The bone implant as defined in claim 1, wherein:
each said projection outwardly protruding from said outer surface of said shaft body having a substantially triangular shape at least in the region close to said at least one edge of such projection;
said triangular shape of each said projection defining a predetermined angle formed at said at least one edge of each said projection; and
said predetermined edge angle assuming a value substantially in the range of about 30° to 150°.

32. The bone implant as defined in claim 31, wherein:
said predetermined edge angle formed at said at least one edge of each said projection assumes a value substantially in the range of about 60° to about 120°.

33. The bone implant as defined in claim 31, wherein:
said predetermined edge angle defined by said at least one edge of each said projection defines an angle substantially in the region of about 90°.

34. The bone implant as defined in claim 26, wherein:
said triangular shape defined by said at least one edge of each said projection has two equal sides.

35. The bone implant as defined in claim 1, further including:
intermediate regions formed between said projections outwardly protruding extending from said outer surface of said shaft body; and
said intermediate regions between said projections being constructed with a substantially round shape.

36. The bone implant as defined in claim 35, wherein:
said intermediate regions between said projections outwardly protruding from said outer surface of said shaft body having a predetermined radius of curvature; and
said predetermined radius of curvature of said substantially round intermediate regions being greater than said edge radius defined by said at least one edge of each said projection.

37. The bone implant as defined in claim 35, wherein:
said intermediate regions formed between said projections outwardly protruding from said outer surface of said shaft body constitute depressions.

38. The bone implant as defined in claim I, wherein:
each said projection of said plurality of projections outwardly protruding from said outer surface of said shaft body defining a predetermined height;
each said projection extending from said proximal end to said distal end of said shaft; and
said predetermined height of each said projection decreasing from said proximal end to said distal end of said shaft.

39. The bone implant as defined in claim 1, further including:
a shaft section arranged at said distal end of said shaft;
said shaft section possessing a generatrix generated outer surface substantially in the shape of a truncated cone;
said generatrix generating said outer surface of said shaft section extending at a predetermined generating angle;
a generatrix generating said outer surface of said shaft body and extending at a predetermined generating angle; and
said generating angle associated with said generatrix generating said outer surface of said shaft section defining a greater generating angle than said generatrix which generates said outer surface of said shaft body.

40. The bone implant as defined in claim 39, wherein:
said shaft section at said distal end of said shaft body assumes a skewed position relative to said shaft body.

41. The bone implant as defined in claim 1, further including:
a substantially cylindrical extension extending at said proximal end of said shaft.

42. The bone implant as defined in claim 38, further including:
an anchoring element provided at said extension extending from said proximal end of said shaft.

43. The bone implant as defined in claim 42, wherein:
said anchoring element of said extension at said proximal end of said shaft constitutes an internal thread.

44. The bone implant as defined in claim 1, wherein:
said shaft body having said outer surface substantially in the shape of the outer surface of a truncated cone, contains, as said inner cavity, at least one substantially cylindrical cavity.

45. The bone implant as defined in claim 44, wherein:
said shaft body contains substantially radially extending connecting passages interconnecting said at least one substantially cylindrical cavity and said bone contact surface of said shaft body.

46. The bone implant as defined in claim 1, further including:
a transitional region;
said distal end of said shaft defining a distal end surface into which opens said inner cavity of said shaft body;
said transitional region extending from said outer surface of said shaft body to said inner cavity opening into said distal end surface; and
said transitional region being constructed to possess an essentially rounded shape.

47. The bone implant as defined in claim 46, wherein:
said essentially rounded shape of said transitional region defining a radius; and
said predetermined radius of said essentially rounded shape assuming a value substantially in the range of 0.2 to 0.8 mm.

48. The bone implant as defined in claim 47, wherein:
said predetermined radius of said essentially rounded transitional region assuming a value of substantially 5 mm.

49. A bone implant for a prostheses, particularly for a joint or joint member of the human locomotor, especially walking system, comprising:
a shaft for insertion into a cavity formed in a bone of the locomotor system;
said shaft including a distal end associated with the diaphysis of said bone and a proximal end associated with the metaphysis of said bone;
said shaft defining a total cross-sectional area which increases form said distal end to said proximal end of said shaft;
said shaft defining a main axis;
said shaft possessing a shaft body of substantially oblong, rotationally symmetric shape defined by a generatrix;
said generatrix generating an outer surface of said shaft body and which contacts the bone;
said outer surface of said shaft body having a plurality of projections extending substantially parallel to said generatrix;
each said projection having at least one edge directed substantially outwardly away from said main axis of said shaft;
further projections extending from said outer surface of said shaft body and arranged between said projections;
said further projections extending from said proximal end of said shaft and terminating at a distance from said distal end of said shaft;
said projections extending from said outer surface of said shaft body and continually extending from said proximal end to said distal end of said shaft, possess a predetermined height;
said predetermined height of said projections being substantially constant through the region from said proximal end to said distal end of said shaft;
said shaft body having a predetermined distal end diameter; and
said projections which continually extend from said proximal end to said distal end of said shaft, being provided in a preselected number which is dependent upon said distal end diameter of said shaft body.

50. The bone implant as defined in claim 49, wherein:
said further projections arranged intermediate said projections which continually extend from said proximal end to said distal end of said shaft body, constitute mutually similar projections.

* * * * *

UNITED STATES PATENT AND TRADEMARK OFFICE
CERTIFICATE OF CORRECTION

PATENT NO. : 4,784,124

DATED : November 15, 1988

INVENTOR(S) : WERNER KALTENBRUNNER et al

It is certified that error appears in the above-identified patent and that said Letters Patent is hereby corrected as shown below:

In the Abstract, line 7, after "preferably," please delete "The" and insert --the--

Column 9, line 2, please delete "shaft'S" and insert --shaft's--

Column 9, line 49, after "well" please delete "s" and insert --as-- and delete "m ember" and insert --member--

Column 10, line 37, after "shown" please insert --)-- (closed parentheses)

Column 12, line 50, after "one" please insert --of--

Column 12, lines 52, please delete "and;" and after "depth" please insert --;and--

Column 12, lines 53 to 56, please delete in their entirety.

Column 13, line 3, after "base" please delete "." (period) and insert --; and--

Column 13, line 61, please delete "main surface" and insert --outer surfaces--

Column 14, line 28, please delete "extending"

Column 14, line 45, please delete "I" and insert --1--

Column 15, line 1, after "which" please delete "." (period)

Column 15, line 49, please delete "5" and insert --0.5--

UNITED STATES PATENT AND TRADEMARK OFFICE
CERTIFICATE OF CORRECTION

PATENT NO. : 4,784,124

DATED : November 15, 1988

INVENTOR(S) : WERNER KALTENBRUNNER et al

It is certified that error appears in the above-identified patent and that said Letters Patent is hereby corrected as shown below:

Column 16, line 10, please delete "form" and insert --from--

Signed and Sealed this

Eleventh Day of July, 1989

*Attest:*

DONALD J. QUIGG

*Attesting Officer*    *Commissioner of Patents and Trademarks*